(12) United States Patent
Matthews et al.

(10) Patent No.: US 12,002,586 B2
(45) Date of Patent: Jun. 4, 2024

(54) ARTIFICIAL INTELLIGENCE SYSTEMS THAT INCORPORATE EXPERT KNOWLEDGE RELATED TO HYPERTENSION TREATMENTS

(71) Applicant: MediSync Inc., Cincinnati, OH (US)

(72) Inventors: Robert E. Matthews, Cincinnati, OH (US); Todd O'Connell, Cincinnati, OH (US); Douglas Romer, Cincinnati, OH (US)

(73) Assignee: MediSync Inc., Cincinnati, OH (US)

( * ) Notice: Subject to any disclaimer, the term of this patent is extended or adjusted under 35 U.S.C. 154(b) by 0 days.

(21) Appl. No.: 18/179,250

(22) Filed: Mar. 6, 2023

(65) Prior Publication Data
US 2023/0207130 A1    Jun. 29, 2023

Related U.S. Application Data

(63) Continuation of application No. 16/546,156, filed on Aug. 20, 2019, now Pat. No. 11,600,388.
(Continued)

(51) Int. Cl.
*G16H 50/20* (2018.01)
*G06N 5/04* (2023.01)
(Continued)

(52) U.S. Cl.
CPC .............. *G16H 50/20* (2018.01); *G06N 5/04* (2013.01); *G16H 20/10* (2018.01); *G16H 50/30* (2018.01); *G06N 20/00* (2019.01)

(58) Field of Classification Search
CPC ........ G16H 50/20; G16H 20/10; G16H 50/30; G06N 5/04; G06N 20/00; G06N 3/08; G06N 7/01; G06N 20/10
(Continued)

(56) References Cited

U.S. PATENT DOCUMENTS 6,000,828 A    12/1999  Leet
9,129,084 B2 *  9/2015  Gogolak ................ G16H 70/40
(Continued)

FOREIGN PATENT DOCUMENTS

EP       4018460 A1    6/2022
WO    2021034938 A1    2/2021

OTHER PUBLICATIONS

Koren et al., Machine Learning Of Big Data In Gaining Insight Into Successful Treatment Of Hypertension, Pharmacol Res Prespect, Apr. 24, 2018, pp. 1-6 (Year: 2018).*
(Continued)

*Primary Examiner* — Joy Chng
(74) *Attorney, Agent, or Firm* — Pillsbury Winthrop Shaw Pittman, LLP

(57) ABSTRACT

Provided is a process, including: obtaining test data that quantifies a patient's cardiovascular status, the test data specifying patient attributes in a plurality of cardiovascular dimensions of the patient; determining a plurality of normalized differences between the test data and target criteria in each of the cardiovascular dimensions; determining predicted-effect vectors of each of a plurality of different classes of pharmaceuticals; determining an aggregate score for each respective class of pharmaceuticals among the different classes of pharmaceuticals based on values of the corresponding predicted-effect vectors; ranking the different classes of pharmaceuticals based on the aggregate scores; and outputting a recommended sequence of pharmaceuticals to administer.

38 Claims, 3 Drawing Sheets

Related U.S. Application Data

(60) Provisional application No. 62/888,928, filed on Aug. 19, 2019.

(51) Int. Cl.
  *G06N 20/00* (2019.01)
  *G16H 20/10* (2018.01)
  *G16H 50/30* (2018.01)

(58) Field of Classification Search
  USPC .......................................................... 706/11
  See application file for complete search history.

(56) References Cited

U.S. PATENT DOCUMENTS

| | | | | |
|---|---|---|---|---|
| 9,530,095 | B2* | 12/2016 | Cao ........................... | G06N 5/02 |
| 11,600,388 | B2 | 3/2023 | Matthews et al. | |
| 2011/0202486 | A1* | 8/2011 | Fung ...................... | G16H 50/70 |
| | | | | 706/46 |
| 2013/0085772 | A1* | 4/2013 | Gaweda .................. | G16Z 99/00 |
| | | | | 705/2 |
| 2020/0135337 | A1* | 4/2020 | Athey ..................... | G16B 30/00 |
| 2020/0273578 | A1* | 8/2020 | Kutzko .................. | G06N 20/00 |
| 2021/0057096 | A1 | 2/2021 | Matthews et al. | |
| 2021/0375455 | A1 | 12/2021 | Matthews et al. | |
| 2023/0207130 | A1 | 6/2023 | Matthews et al. | |

OTHER PUBLICATIONS

Wanger et al., "Algorithms for optimizing drug therapy," BMC Med Inform Decis Mak. Jul. 20, 2004;4:10. doi: 10.1186/1472-6947-4-10. PMID: 15265240: PMCID: PMC493275 (Year: 2004).*

European Search Report for related European Patent Application 20854532.7 dated Jul. 24, 2023, 6 pages.

Koren Gideon, et al., "Machine Learning of Big Data in Gaining Insight into Successful Treatment of Hypertension," Pharmacology Research & Perspectives, vol. 6, No. 3, Apr. 24, 2018, pp. 1-6.

Office Action for related Canadian Patent Application 3148622, dated Oct. 12, 2023, 3 pages.

* cited by examiner

ARTIFICIAL INTELLIGENCE SYSTEMS THAT INCORPORATE EXPERT KNOWLEDGE RELATED TO HYPERTENSION TREATMENTS

CROSS-REFERENCE TO RELATED APPLICATIONS

The present patent application is a continuation of U.S. patent application Ser. No. 16/546,156, titled ARTIFICIAL INTELLIGENCE SYSTEMS THAT INCORPORATE EXPERT KNOWLEDGE RELATED TO HYPERTENSION TREATMENTS, filed 20 Aug. 2019, which claims the benefit of U.S. Provisional Pat. App. 62/888,928, titled ARTIFICIAL INTELLIGENCE SYSTEMS THAT INCORPORATE EXPERT KNOWLEDGE RELATED TO HYPERTENSION TREATMENTS, filed 19 Aug. 2019. The entire content of each afore-mentioned patent filing is hereby incorporated by reference.

BACKGROUND

1. Field

The present disclosure relates generally to artificial intelligence (AI) and, more specifically, to AI systems that incorporate expert knowledge related to the management and care of patients with hypertension while retaining the ability to generalize to provide appropriate responses to novel inputs.

2. Description of the Related Art

Physicians and other medical practitioners contend with an enormous amount of complexity when treating patients. A significant amount of that complexity is involved in selecting the medications that can best help a specific patient and that patient's vast array of specific variables. Often, doctors have to make decisions under uncertainty based upon relatively noisy, high dimensional data about patients, and those signals can evolve over time, and some cases in ways that are difficult to predict.

Medical practitioners are trained in and are taught to know and apply an enormous body of medical research to select the appropriate interventions for patients. At this point in time there are approximately 800,000 new medical journal articles published per year. In order to win Food and Drug Administration (FDA) approval every medication must be tested in studies that are carefully constructed and executed under FDA supervision and approval. Subsequent studies of the same drug may occur under independent auspices or sponsored by the drug manufacturer. Each study has a certain set of inclusionary and exclusionary variables. Different studies of the same drug can and often do have different inclusion and exclusion variables and values. When physicians go to prescribe a drug, it is unlikely that they can recall from memory which studies investigated that condition or that drug and extremely unlikely that to recall any of the inclusion and exclusion variables. Thus, determining which drug to use is very difficult.

To assist those in the field, on occasion teams of experts are convened under the authority of different national or international authorities like the American College of Cardiology, the American Heart Association, the Institute of Medicine, etc. to sort out the various studies related to a specific disease state and to update the science that is available with regard to that disease state concluding with high level findings. After hundreds of thousands of pages of published scientific papers, for example, a body might establish a standard of care sometimes called "The Evidence Based Standard of Care" (EBS). At a minimum an EBS or another standard will define, in some fields, a standard by which successful therapy or treatment can be measured, e.g., a goal for therapy and general comments about a variety of tools one could use to achieve that goal. But these standards can be challenging to implement, become out of date, or apply less granular heuristics to favor administrability over precision.

Given these challenges, only very recently have developers and computer science researchers begun to attempt to help doctors choose the appropriate course of treatments for patients, and many of these attempts to date have been limited to diseases like cancer. These attempts, however, have not been met with success generally. Some approaches have attempted to apply expert systems that encode the universe of medical knowledge in a collection of rules. The problem with rules are that the number of variables combined with the way that variables can interact and the number of solution options can approach tens of millions of permutations, which is beyond the capability for rule making. In general, expert systems have proven too brittle, unable to generalize outside of scenarios explicitly contemplated by the system architect. Such systems often struggle with patients presenting novel scenarios. On the other hand, some researchers have attempted to train models with relatively large numbers of degrees of freedom, like deep neural networks, on historical records of treatments and patient responses. These systems, however, often fail to benefit from the knowledge produced by medical research and in many cases have a relatively low training efficiency. These models struggle with smaller training sets and training sets in which samples are sparse in areas in which the model may be later requested to perform. There is also the problem that medical data is often extremely noisy and filled with error.

SUMMARY

The following is a non-exhaustive listing of some aspects of the present techniques. These and other aspects are described in the following disclosure.

Some aspects include a process including: obtaining, with a computer system, data from one or multiple tests that, for example, quantifies a patient's cardiovascular functional status, the test data specifying patient attributes in a plurality of cardiac, vascular and cardiovascular dimensions of the patient, a first subset of the plurality of cardiovascular dimensions being independent cardiovascular dimensions and a second subset of the plurality of dimensions being dependent cardiovascular dimensions; determining, with the computer system, a plurality of normalized differences between the test data and target criteria in each of the cardiovascular dimensions, the plurality of normalized differences quantifying different aspects of hypertension of the patient; determining, with the computer system, predicted-effect vectors of each of a plurality of different classes of pharmaceuticals having hypertension as an indication, wherein: the predicted-effect vectors each correspond to a different respective class of pharmaceuticals among the different classes of pharmaceuticals, the predicted-effect vectors each have a plurality of values quantifying respective effects of the corresponding class of pharmaceuticals on corresponding dimensions among a third set of the cardiovascular dimensions of the patient, the values are each based on both the corresponding normalized differences of the corresponding dimension among the third set and a respective strength of effect of the corresponding class of pharmaceuticals on the corresponding dimension, the respective strength effects are determined based on respective multi-dimensional models of the corresponding class of pharmaceuticals, and the third set at least overlaps with the first subset and the second subset; determining, with the computer system, an aggregate score for each respective class of pharmaceuticals among the different classes of pharmaceuticals based on values of the corresponding predicted-effect vectors of the corresponding class of pharmaceuticals; ranking, with the computer system, the different classes of pharmaceuticals based on the aggregate scores to form a ranked list of the different classes of pharmaceuticals; and outputting, with the computer system, based on the ranking, a recommended sequence of the classes of pharmaceuticals to administer to the patient.

Some aspects include a tangible, non-transitory, machine-readable medium storing instructions that when executed by a data processing apparatus cause the data processing apparatus to perform operations including the above-mentioned process.

Some aspects include a system, including: one or more processors; and memory storing instructions that when executed by the processors cause the processors to effectuate operations of the above-mentioned process.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
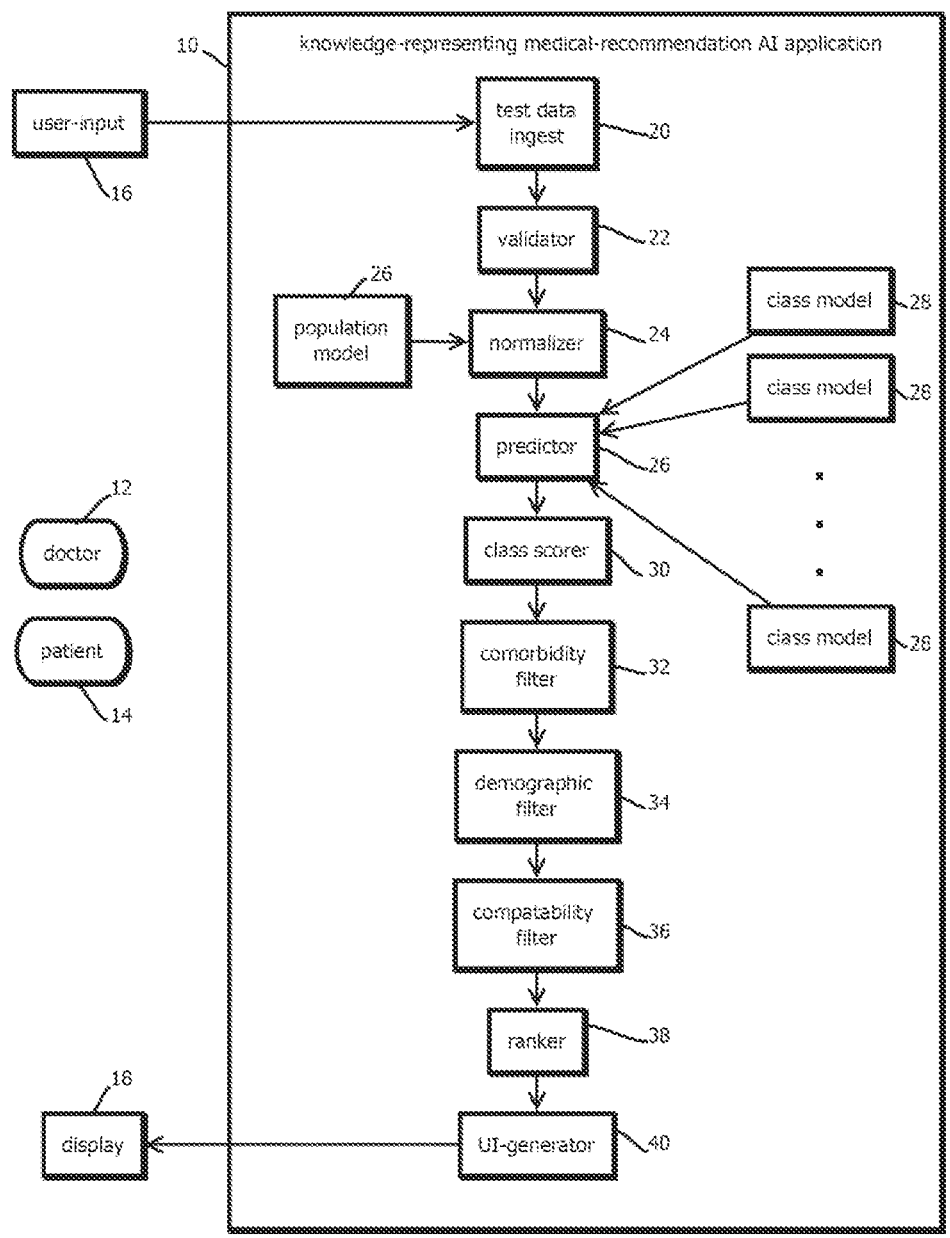
FIG. 1 is a logical architecture block diagram of a knowledge-representing medical-recommendation AI application in accordance with some embodiments of the present techniques.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the field of artificial intelligence. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Some embodiments mitigate some of the above-described issues with an artificial intelligence application that encodes knowledge from medical research in a collection of models responsive to patients states in relatively large envelopes of relatively high dimensional patient-state spaces. As a result, the models are expected to be less brittle than rules in an expert system, while still capturing medical knowledge from relevant literature in the field. Further, the models are expected to be more training-data efficient than naïve applications of machine learning models that do not benefit from expert knowledge. None of which is to suggest that use of the present techniques in conjunction with expert systems or such machine learning models is disclaimed or the any other subject matter discussed herein is disclaimed.

The present techniques are described with reference to recommending interventions for hypertension, but it should be emphasized that the present computing techniques are expected to have application in a wide variety of fields having similar properties to the discussed use cases. As recently as thirty-years ago there were few medications to treat hypertension and many patients died or suffered major complications (e.g., strokes, heart attacks, Transient Ischemic Attacks (TIAs), renal failure, etc.) caused by their uncontrolled blood pressures. In those days the physician would try the few available drugs to reduce blood pressure. Often, though, blood pressure could not be controlled.

Over the intervening years there has been enormous research into hypertension—and most of the other, common chronic diseases—resulting in a deeper, more complex understanding about the diseases, their causes and various factors or variables related to those disease. The additional knowledge, in turn, resulted in the development of many more therapies. In 2019 there are more than twelve classes of drugs that can be used to treat hypertension and, within, those classes, there are often multiple different drugs per class, each slightly different from the others within the same class.

As mentioned, an EBS or other standard may define a standard by which successful therapy or treatment can be measured, e.g., a goal for therapy and general comments about a variety of tools one could use to achieve that goal. For instance, in hypertension, a blood pressure of ≤139/89 (also expressed as <140/90) is considered controlled and a blood pressure that is ≥140/90 is considered "uncontrolled" and therefore more dangerous to the patient by several authorities. Other authorities have argued persuasively for a blood pressure as low as <130/80, so there is no universal consensus in some cases.

The Centers for Disease Control (CDC) states that a goal of <140/90 is a minimal standard for control of hypertension. The Centers for Medicare and Medicaid (CMS) requires that providers must report the percentage of all their adult patients who are less than 85 years old with a diagnosis of hypertension that are below 140/90 and this is percent is a measure of physician success as a treater of hypertension. The CDC also reports that only about half of US patients with hypertension achieve the safer level of blood pressure <140/90.

A blood pressure reading typically includes both the systolic and diastolic blood pressure (i.e., systolic/diastolic). These are high order measures. The systolic and diastolic pressures are the result of a cascade of "cause and effect" relationships. Not all of these relationships are completely understood or known by medicine but many are. For example, blood pressure is determined in part by various performance characteristics of the heart, blood vessels and fluid status. The heart's functions, blood vessel functions or the fluid status of the patient are, in turn, influenced or determined by many neuro-hormonal, bio-chemical, mechanical, age, race, genetic and other variables.

It is possible to treat a patient in a manner that the desired end point blood pressure is achieved but other cardiac, vascular, fluid variables are unacceptably out-of-range. In such an instance the patient's care is sub-optimized despite having a "good" blood pressure (e.g., below 140/90) because, while the overall blood pressure meets the EBS of care, the underlying parameters are not ideal. This can occur, for instance, when one variable is over-treated and another variable undertreated resulting in an "average" blood pressure that is at the acceptable levels. In these instances, there may be ongoing harm to the patient's overall current or future health status despite the blood pressure being in the desired range.

Another set of variables is that a specific patient with high blood pressure may have any of a significant number of comorbidities which can individually or in combination determine which therapies can or cannot be used effectively or safely. There are a variety of potential effects of co-morbidities to a treatment strategy including:
  a. Co-morbidities can promote the use of certain agents or therapies;
  b. Co-morbidities can alter the therapeutic characteristics of agents or therapies rendering them more or less effective;
  c. Co-morbidities can eliminate the possibility of using certain therapies;
  d. Co-morbidities can change the prioritization or order of using therapies;
  e. Co-morbidities can cause certain potential problems which then have to be evaluated as therapies are added; and
  f. Co-morbidities can alter or change entirely the therapeutic end-points for a disease.

In some instances, the effect of one co-morbidity points therapy in one direction while a second co-morbidity points therapy in the opposite direction and this conflict must be resolved based upon some evaluation of the weight of various factors.

The evolution of scientific knowledge that has resulted in recognition of all these patient attributes that drive blood pressure has led to the multiplication of therapies including the hundreds of drugs that exist today but did not even thirty or fewer years ago.

Thus, treating hypertension implicates the above-described complexity. It is worth keeping in mind that, as of 2019, there are over 800,000 scientific medical articles published per year. This is a tremendous amount of information for a human-actor to absorb. In blood pressure treatment, the role of the physician or other licensed care provider is to calculate all or as many of the above-mentioned variables as possible in order to determine both effective as well as optimal therapy for a specific patient. There are literally tens of millions of permutations involved when you consider all the cardio-vascular, demographic, pharmacological and co-morbid conditions. This complexity is more than even a very intelligent person can manage in her head. It is believed that this is an underlying reason why the success rate in hypertension is as low as 50% on average.

What happens often is that patients who present with the most common forms of hypertension and who do not have a lot of complications or co-morbidities are most likely to be successfully treated while the more complex cases are very often unsuccessfully treated.

To manage this level of extreme complexity, some embodiments implement an AI system described below with reference to FIGS. 1 and 2 on one or more computing devices like that described below with reference to FIG. 3. Some embodiments obtain each specific hypertension patient's "starting point"—e.g., all of the medically-available variables that influence the patient's current blood pressure state—and then determine a (often multi-step) route to the desired outcome (e.g., an end point blood pressure, aligning the other cardiac, vascular and fluid metrics and take into consideration all of the comorbidities) via optimal medication therapy.

Embodiments determine this route in a different way from previous applications of AI to recommend medical interventions. A rules engine, standing alone, is believed to be unsuitable for this task. The variety of permutations of patient states is simply too large, making an expert system brittle to the type of novel inputs expected to be encountered with regularity. Also, a commercially-feasible rules engine would not be able to consider various combination or interaction effects which also arise.

Embodiments determine this route through what is believed to be a fundamentally different approach to how a human would undertake the analysis. General AI is not available, and there is no documented algorithm universally implemented by physicians. The way humans make these decisions is believed to be based on some combination of Bayesian analysis and rough heuristics as a short-cut for accounting for the available knowledge in the field. The result, as an empirical matter, is sub-optimal, and inferior to results obtained with the present techniques. As such, the present is necessarily different, in part because it is more performant, in part because it is more comprehensive, and in part because of the way knowledge in the field is systematized by models to make that knowledge usable to an AI system across a wide range of high-dimensional novel (in the sense that the state has not been input to the system before or was not part of a training set) patient-state inputs.

In some embodiments, the physiological status including heart function, vascular functions, vascular compliance and fluid levels may be determined. Many of these variables may be evaluated and measured as functions of each other. Thus, some variables are not absolute measures, common to all patients, and there is a combinatorial explosion of possible patient states when all medically useful variables are evaluated.

Some embodiments implement a cardiovascular model to define the cardiac, vascular and fluid forces in relationship to each other and as outcomes. With such models, measured patient attributes may be transformed into other estimated or otherwise inferred patient attributes, in some cases based on interactions of measured patient attributes, patient demographic attributes, and comorbidities.

Some embodiments implement a drug-efficacy model that quantifies the effectiveness and other performance characteristics of each drug or drug combination against each of the various patterns generated by the cardio-vascular model as generated in the first step.

Some embodiments implement a comorbidity model to quantify the implications of over 25 comorbidities and other factors that can change recommendations in various ways.

Some of these models may implement one or more performance curves to quantify the effects of a specific given variable and interactive performance curves quantifying the effects of one or several variables collectively or on a one-to-one basis.

In some embodiments, test data, such as diagnostic test data, are used by the computer system to quantify the patient's cardiovascular status. The data may be plotted against multiple cardiovascular measurement scales. These measurement scales may be mathematically related to each other in many cases. A subset may be independent. In some embodiments, four independent variables are the only inputs into drug class scoring: systolic blood pressure (S), pulse pressure (p), cardiac index (x), and heart rate (z).

The relative distances between the patient datum (or other collection of attributes collectively representing patient state) and multiple target criteria may be calculated to quantify the different aspects of hypertension. The various criteria may be heterogenous units-of-measure and have dramatically different scales. That is, for one measure values are commonly between 0.25 and 0.95, whereas another measure is between 1500 and 6000. A scale rationalization (or other form of normalization) technique may be used to quantify the relative comparative magnitude of distances, resulting in all measures on a shared scale (e.g., of −3.0 to +3.0). In some embodiments, the shared scale may be a number of standard deviations from target, like a mean of a population from which the standard deviation is determined, like a z-score. A negative distance meaning below or less than target and a positive distance meaning above or greater than target.

The test data may be processed to provide a patient's status, indicating the most important aspect of their hypertension and which variables need to move most and in which direction (increase/decrease).

In some embodiments, drug-efficacy models may be constructed to accommodate the fact that different pharmaceutical agents or classes affect different cardiovascular parameters. An analyses of the literature and consultation with pharmacology specialist about best methods to interpret discrepancies could be used to construct a weighted scoring system, which may be applied to reflect the efficacy of the drug class on a particular parameter. Example weights may be stored in a matrix with columns corresponding to drug class and rows corresponding to various cardiovascular parameters, like V, C, z, and Si. Different drug classes may have different weights for different cardiovascular parameters. An example of such a matrix is presented in the following table:

| HTN drug class weighting scores | | | |
|---|---|---|---|
| parameter | drug class A | drug class B1 | drug class Cn |
| V | 4 | 0 | 3 |
| C | 0 | 3 | 4 |
| z | 0 | 4 | 2 |
| Si | 0 | 2 | 1 |

The resulting score for a particular hypertension drug class may be the quantification of the cumulative net beneficial effect, which may be computed with a variety of approaches, such as a weighted sum of the strength of effect times the distance for each cardiovascular parameter. This approach may be used to score the various hypertension drug classes in a nearly-orthogonal array of possible patient data. With this approach, in some embodiments, models may be implemented for each drug class. In some cases, the models may correspond to four or five or higher dimensional non-planar surfaces with one output dimensions and several input dimensions corresponding to patient attributes.

With these models, some embodiments determine an aggregate a score for each drug class given a unique set of independent inputs for the patient. These scores may then be compared to each other to determine the optimum hypertension drug treatment regimen.

Two additional processes may be applied by some embodiments to generate the "ladder" of drug classes. The concept of the ladder is based on evidence that it often requires more than one drug class to effectively control hypertension. Additionally, often a patient is already taking the recommended drug class. The provider then would decide to increase the dosage of the top recommended drug class or add the next highest recommended drug class. In some cases, a ladder may be expressed as a sequence, which may specify one or more stages in which, during each stage, one or more classes of drugs is to be administered to the patient.

Most hypertension drug classes can be safely taken together. However, some combinations of drug classes should not be taken together. For example, drug classes Cd and Cn should not be taken together; same for drug classes B1 and B3. The resulting list may be filtered to skip over drug classes that are not to be taken in combination. The higher scoring drug class may be the only one of a pair in conflict allowed to remain on the ladder.

In some embodiments, the cardiovascular scores may be modified given the presence of certain comorbidities or demographic information about the hypertension patient. Some hypertension drug classes are contraindicated for specific medical conditions. For example, a given drug class A may be contraindicated for pregnancy. In other cases, a drug class may have a very beneficial effect on a given comorbidity. For example, drug class A may have a positive influence when renal function or diabetes are present. In response to input indicating a potential comorbidity or related attribute, drug class scores of corresponding drug classes may be adjusted accordingly. And in some cases, multiple clinical conditions could be present and all have additive adjustments to the final drug class score and its associated ranking in the ladder.

In some embodiments, the above techniques and related techniques may be implemented in a computing environment shown in FIG. 1. A knowledge-representing medical-recommendation AI application 10 may execute on one of the computing devices described below with reference to FIG. 3, for example, in an operating system thereof, or on a collection of such computing devices, for example, with various components implemented as services in a service-oriented architecture. Or in some cases, the application 10 may be executed as a monolithic application on a single computing device, for example, as a single process run on a single processor core.

In some embodiments, the application 10 may be configured to receive input from a doctor 12 about a patient 14 via a user input 16. In some embodiments, the application 10 may be configured to cause a presentation of information responsive to the input on a display 18, like a graphical user interface on a monitor, head-mounted display, or the like, or via an audio display via speech-to-text conversion of outputs to audio conveyed via a speaker. Or in some embodiments, the display 18 is implemented with a printer printing a printed page with outputs.

The input 16 may include a keyboard, a microphone coupled to a speech-to-text translator, a touchscreen, a mouse, or an application program interface of another application providing a set of inputs to the application 10, for example, a patient record database configured to export patient medical records to the application 10 responsive to a query from the application 10 or other instructions from a medical practitioner.

In some embodiments, the application 10 may execute on a computing device in a doctor's office or hospital, and inputs and outputs may be received and provided without conveying information over a network for security purposes, or in some cases, the application may be remotely hosted and information may be conveyed while encrypted in transit.

In some embodiments, the application includes a test data ingest module 20 configured to receive a patient record indicating a medical state of the patient at a given point in time. In some embodiments, the ingest module 20 may be configured to receive a plurality of such records corresponding to a history of states of the patient, each record having a timestamp indicating a time at which the state was exhibited by the patient. In some embodiments, the records may include a plurality of attributes of the patient related to hypertension in various cardiovascular dimensions.

Some of the dimensions may be independent dimensions, like those listed above, and some of the dimensions may be dependent the dimensions that are caused, at least in part, by the independent dimensions, and some cases through interactions thereof. Examples of such dimensions include the following:

S=systolic blood pressure (SBP)
D=diastolic blood pressure (DBP)
p=pulse pressure (SBP−DBP)
y=mean arterial pressure (MAP=DBP+?p)
x=cardiac index (CI)
z=heart rate (HR/pulse {bpm})
V=total peripheral resistance index (TPRI=80*MAP/CI)
C=cardiac power index (CPI=0.0022*MAP*CI)
Si=stroke index (SI=1000*CI/HR)

In some embodiments, attributes of the patient and each of these dimensions may be entered into a user interface presented on the display 18, for example, in fields of the form by a medical technician after having measured the various attributes of the patient. Or in some cases, the attributes may be received via an application program interface from another application, for example, in hierarchical data serialization format.

In some cases, a set of received attributes may be transformed into a larger set of inferred attributes of the patient based on a patient model like those discussed above. For instance, some such models may model the patient with a causal graph, with input nodes corresponding to observable attributes and edges and downstream causal nodes specifying transformations by which other patient attributes may be inferred, in some cases, based on interactions of observed or computed patient attributes.

Some embodiments may validate the patient record with validator 22. In some embodiments, this may include determining that all required attributes (i.e., a value in a dimension) are present, that the received attributes are greater than a minimum possible value, and that the received attributes are less than a maximum possible value in the respective dimension. Upon determining that a given patient attribute is outside of one of these ranges, some embodiments may emit an error message and present an input via display 18 inviting a medical professional to confirm that the value is correct or change the entry via input 16. Some embodiments may determine whether an attribute in a patient record is more than a threshold amount different from a previous attribute in the same dimension in a previous record, with outlier differences potentially indicating an erroneous entry. Again, some embodiments may signal and alarm and invite correction responsive to detecting such an event.

In some embodiments, after all of the patient record attributes are validated, the result may be advanced to the normalizer 24 in the illustrated pipeline of the application 10. In some embodiments, the normalizer 24 may compute normalized differences between each patient attribute and a target value of that attribute in the attributes dimension. In some embodiments, these differences may be quantified relative to population statistics of the respective attribute in a population, as reflected in the population model 26. For example, the normalized attribute may be expressed as a z-score indicating an amount of standard deviations above or below a mean for the attribute in a population, as encoded in the population model 26. Some embodiments may compute similar statistics for other types of non-Gaussian distributions. Some embodiments may compute a percentage of the population that is above the patient's attribute as measured in the given dimension and subtract 50 percentage points to center the result around zero. In some embodiments, normalized values for each attribute may have a negative value to indicate that the patient's attribute is lower than is desired and a positive value to indicate that the patient's attribute is higher than is desired. In some embodiments, the normalized values may all be on the same scale, despite having measured attributes in the patient record on different scales. In some cases, values may be normalized after subsequent transformations described below, e.g., class models 28 described below may be calibrated to non-normalized values, and outputs thereof may be normalized to facilitate combination of values across various attributes with heterogenous units-of-measure and ranges.

In some embodiments, the population model 26 may characterize population statistics of attributes in each of the dimensions of the patient record. The characterization may take a variety of forms, including a histogram, a measure of central tendency (like mean, median, and mode) and a measure of variation (like standard deviation or variance). In some embodiments, the measure of central tendency may be a target value for the respective dimension of the patient's cardiovascular health. In some embodiments, the population may be a known healthy population or reference population. In some cases, the target value may be determined from the above-described EBS.

The output of the normalizer 24 may be a normalized patient record having a plurality of normalized attributes in a plurality of different cardiovascular dimensions. For example, the normalizer 24 may output more than four, more than six, or more than eight normalized values ranging from −3 to +3 and each corresponding to a different cardiovascular dimension of the patient.

The output of the normalizer 24 may be provided to a predictor 26, which may predict magnitudes and directions of effects of various classes of pharmaceuticals that indicate for hypertension on the respective attributes in the corresponding dimensions of the patient's cardiovascular health. For example, the predictor may predict that a first class of pharmaceuticals will decrease a first normalized attribute by a first amount on the normalized scale and increase a second normalized attribute by a second amount on the normalized scale, while a second class of pharmaceuticals may be predicted to decrease the first normalized attribute by a third amount on the normalized scale, have no effect on the second normalized attribute, and decrease a third normalized attribute by a fourth amount on the normalized scale.

In some embodiments, the predictor 26 may determine a set of predictions for each of a plurality of different classes of pharmaceuticals that indicate for hypertension. For example, nine different predictions for nine different cardiovascular dimensions may be determined for a first class of pharmaceuticals, and nine different predictions for the same nine different cardiovascular dimensions may be determined for a second class of pharmaceuticals. In some embodiments, each set of predictions may be characterized as a predicted-effect vector, which may specify a location in a continuous vector space or discrete vector space corresponding to the cardiovascular dimensions of the patient. Program state need not be labeled as a vector in program code to constitute a vector, provided that the information of a vector is encoded. In some embodiments, the dimensions for which a prediction is made may be the same as those for which data is obtained by the ingest module 20, or in some cases predictions may only made for a subset of those dimensions, such as just the independent cardiovascular dimensions.

In some embodiments, each predicted-effect vector may have a plurality of values corresponding to predicted effects in each of the different cardiovascular dimensions of the patient. In some embodiments, the values may indicate whether the predicted effect tends to drive the corresponding attribute closer to the target in the cardiovascular dimension or further from the respective target. For example, an attribute that is below the target, but for which a predicted effect tends to increase the attribute to be closer to the target, may have a value that is positive, while an attribute that is above the target and for which the predicted effect tends to increase the attribute may have a value that is negative. In some embodiments, the resulting value may be a difference between an absolute value of the attribute in the normalized record and an absolute value of the attribute predicted to occur upon application of the class of pharmaceuticals at issue. Making an attribute further from his target become closer to his target may tend to correspond with a larger value and vice versa.

In some embodiments, the predictor 26 computes the predicted-effect vector based upon a corresponding one of the class model 28. In some embodiments, each class model 28 corresponds to a different class of pharmaceuticals, or in some cases interactions between classes of pharmaceuticals may also have their own class model. In some embodiments, each class model encodes a three, four, five, six, seven, or higher dimensional surface, indicating effects of the corresponding class of pharmaceuticals in each of the cardiac dimensions for which predictions are made based upon the normalized state of the patient received from the normalizer 24. In some cases, these higher dimensional models may be decomposed into lower dimensional slices, like a plurality of different three-dimensional or four dimensional representations, which collectively still constitute the higher dimensional model regardless of the lower dimensional encoding. In some cases, the models have an output dimension in each of the above-described cardiovascular dimensions and an input dimension in each of the above-described cardiovascular dimensions. The surface may indicate how inputs map to outputs for the respective class of drugs. The models may be formed by synthesizing medical research, e.g., averaging empirical data across studies, training a Markov chain Monte Carlo model with empirical results of such studies, based on application of results of one study to a model proven by another, interpolating between regimes examined in different studies, or the like. The models 28 may take a variety of forms. Examples include polynomial functions, or collections thereof. Other examples include lookup tables, support vector machines, neural networks, and other lossy or lossless encodings of relationships between inputs and outputs.

In some case, a predicted effect matrix may be computed for each class of pharmaceuticals, with drug-specific predicted-effect vectors for drugs within the class. Models 28 may be developed for different members of a class. In some cases, a highest scoring drug within a class (based on the following analysis) may be selected as the predicted-effect vector for that class, and that specific member of the class may be recommended.

In some embodiments, the predicted-effect vectors for each of the different classes of pharmaceuticals may be output to the class scorer 30, which may compute an aggregate score (e.g., a single ordinal or cardinal value) for each of the classes of pharmaceuticals based on some or all of the values in the respective corresponding predicted-effect vector for that class of pharmaceuticals. Or in some embodiments, scores may be computed for a plurality of different metrics, or some embodiments may compute a single aggregate score for each class, which in some cases may be a sum of the computed values that serve as scalars of the predicted-effect vector, or in some cases the aggregate score may be a weighted sum of these values. Weights may be determined with a variety of techniques, including hand coding weights based upon knowledge of an expert in the field or empirical literature in the field. The class scorer 30 may output a set of aggregate scores, e.g., with one aggregate score for each of the different classes of pharmaceuticals. The aggregate scores may indicate a preliminary suitability of the respective class of pharmaceuticals for the patient, with larger scores indicating greater suitability and lower scores indicating lower suitability. (Reference to signs of scores and other values should be read as also referring to semantic equivalents in which signs are inverted, for example, discussion of a score in which a higher value indicates a desirable result should be read as equivalent to discussion of a negative version of that score or an inverse of that score in which a lower value indicates the desired result.)

The set of scores for the class of pharmaceuticals may be received by the comorbidity filter 32. In some embodiments, the scores may be adjusted based upon various comorbidities of the patient. For example, certain classes of pharmaceuticals may be documented in the literature as having a negative effect or being precluded for patients having a particular comorbidity, or some classes of pharmaceuticals may be more desirable for some comorbidities. In some embodiments, the relationships may be encoded as adjustment factors, such as sums added to the scores or weights multiplied by the scores. For instance, a patient being pregnant may cause a particular class of pharmaceuticals score to be multiplied by 0.8 to indicate that the class of pharmaceuticals can have negative effects, while another class of pharmaceuticals score may be multiplied by 0 indicate that pregnant women are not to take that class of pharmaceuticals. The term filter is used to refer to this process of adjustment, which in some cases may take the form of removing candidate classes of pharmaceuticals or in other cases may take the form of transforming the scores upon which those classes of pharmaceuticals are selected among.

Some embodiments may similarly apply a demographic filter 34, which may apply similar adjustments based upon demographic attributes of the patient, like race, gender, age, and the like.

Some embodiments may apply a compatibility filter 36 to the classes of pharmaceuticals. Some embodiments may maintain a square matrix or other data structure encoding pairwise comparisons between the candidate classes of pharmaceuticals with matrix values indicating whether the different pairs of classes of pharmaceuticals indexed to those entries are compatible with one another. Or some embodiments may encode a weight or sum to be applied as an adjustment to the above-describe scores when the pairs of pharmaceutical classes are used together (e.g., concurrently, sequentially, or as part of the same sequence even if not sequentially, and some embodiments may apply a different compatibility matrix to each of these different types of relationships between classes of drugs in a course of treatment, for instance to identify those that may be grouped for concurrent use or should be taken sequentially). Some embodiments may detect pairs of pharmaceuticals that are not compatible and remove from the candidate set a lower ranking member of the pair.

Some embodiments may implement a ranker 38 that may rank the resulting adjusted or otherwise filtered classes of pharmaceuticals based on the scores as transformed by components 30 through 36. In some embodiments, the operations implemented by these components may be executed in a different order from that depicted in the illustrated pipeline, which is not to suggest that any other feature is limited to the arrangement shown. In some cases, ranking may include grouping classes of pharmaceuticals to be taken concurrently, and in some cases, it may include indicating groups of one or more to be taken serially, according to rank, e.g., starting from a highest-ranking class and working downward.

Some embodiments may then pass the resulting ordered list from the ranker 38 to the user interface generator 40, which may generate a user interface displaying the results through any of the types of displays above on display 18. In some embodiments, in the user interface, various classes of pharmaceuticals may be further annotated with data about specific vulnerabilities or suitability of the patient for the class of pharmaceuticals. For example, where a comorbidity causes an aggregate score for a class of pharmaceuticals to be adjusted, in response, a prose description of the adjustment and rationale may be retrieved from memory and presented in association with the class pharmaceuticals in the user interface. Similarly, where classes of pharmaceuticals are prohibited or are incompatible, prose descriptions of warnings may be retrieved from memory in response to detecting that such events have occurred and presented in the user interface by the user interface generator 40.

Figure 2:
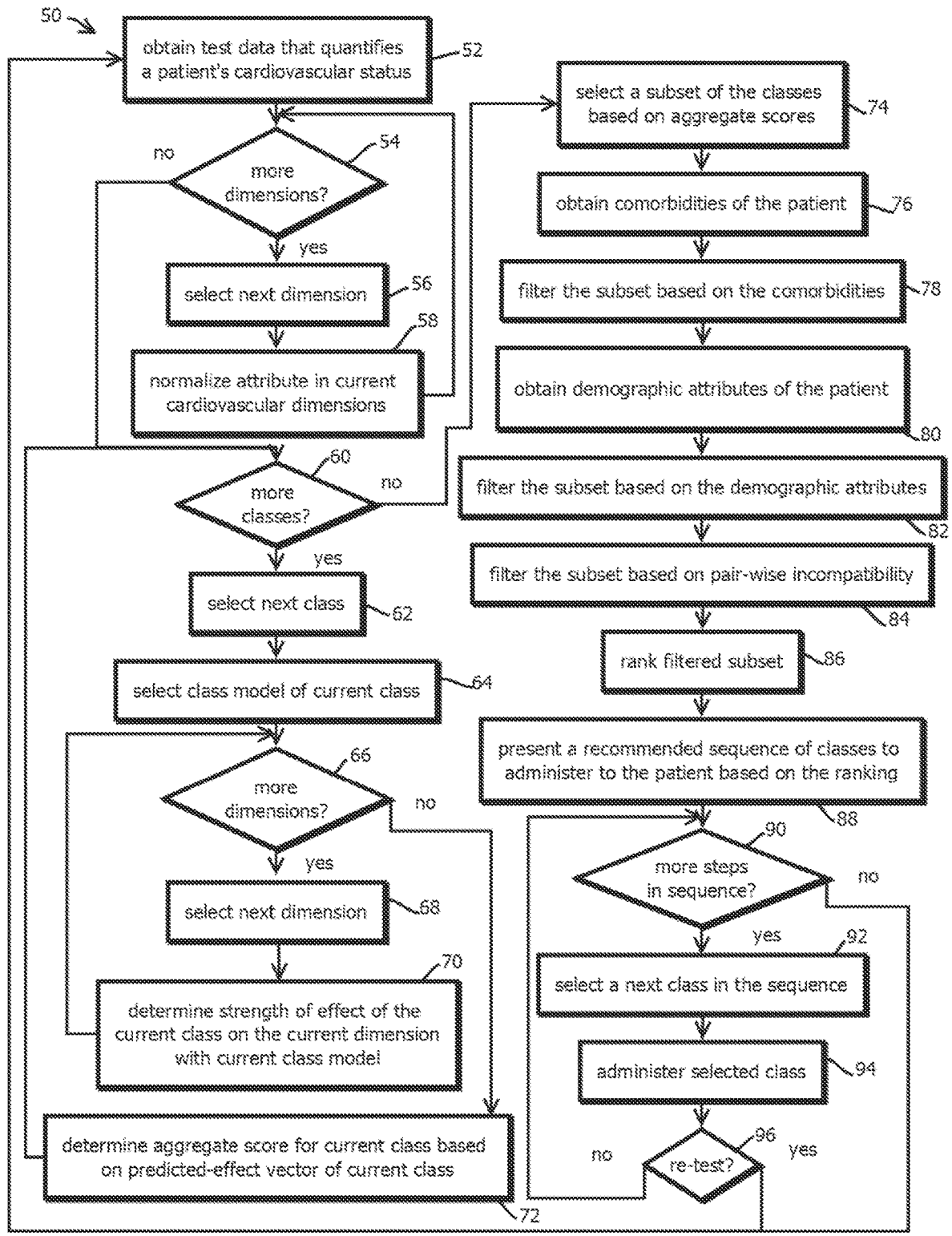
FIG. 2 is a flowchart of a medical-intervention recommendation process for hypertension that may be implemented with the logical architecture of FIG. 1 in accordance with some embodiments of the present techniques.

In some embodiments, the application of FIG. 1 may execute a process 50 shown in FIG. 2 to recommend a course of interventions for hypertension, though embodiments of the process 50 are not limited to that implementation, which is not to suggest that any other feature described herein is limiting in all embodiments. In some embodiments, the functionality of the process 50 and the other functionality described herein, with the exception of administering treatments, may be implemented as computer code stored in a tangible, non-transitory, machine-readable medium and executable on one or more processors, such that when that computer code is executed, the corresponding functionality is effectuated. In some embodiments, the described operations may be executed in a different order, additional steps may be inserted, some steps may be executed concurrently, some steps may be omitted, some steps may be repeated multiple times before advancing to other steps, and the process may otherwise be varied, which again is not to suggest that any other description herein is limiting.

Some embodiments of the process 50 include obtaining test data that quantifies a patient's cardiovascular status, as indicated by block 52. In some embodiments, this may include obtaining the above-described patient record. In some embodiments, this patient record may be computed in part by applying measured attributes to a patient model to compute dependent variables of the patient's cardiovascular health, for example, with a patient model configured to map those inputs into a corresponding output.

Some embodiments may determine whether there are additional dimensions in the test data, as indicated by block 54. Upon determining that there are additional dimensions, the process 50 in some embodiments may select the next dimension, as indicated by block 56. Some embodiments may then normalize an attribute in the current cardiovascular dimension, as indicated by block 58, for instance, with the above-described normalization techniques. Embodiments may then return to block 54 and determine whether there are more dimensions in the test data process. Upon determining that there are no more, some embodiments may proceed to block 60 and determine whether there are more classes of pharmaceuticals to process. Upon determining that there are, some embodiments may select the next class, as indicated by block 62.

Some embodiments may then select a class model of the current class, as indicated by block 64, for instance, among the above-described class models 28 in FIG. 1. Some embodiments may then determine whether there are more dimensions of a predicted-effect vector to process, as indicated by block 66. Upon determining that there are more dimensions, some embodiments may select the next dimension of the predicted-effect vector being computed, as indicated by block 68. Some embodiments may then determine a strength of effect of the current class on the current dimension with the current class model, as indicated by block 70. Embodiments may then return to block 66 to determine whether there are more dimensions of the predicted-effect vector to process with the current class model.

Upon determining that there are no more dimensions the process, in some embodiments, may proceed to select a subset of the classes based on the aggregate scores, as indicated by block 74. Some embodiments may then obtain comorbidities of the patient, as indicated by block 76, and filter the subset based on the comorbidities, as indicated by block 78. Again, filtering, as that term is used herein, may include adjusting respective scores or removing from further consideration some classes of pharmaceuticals. Some embodiments may then obtain demographic attributes of the patient, as indicated by block 80, and filter the subset based on the demographic attributes, as indicated by block 82, for instance, with the techniques described above. Some embodiments may further filter the subset based on pairwise incompatibility, as indicated by block 184, for instance, with the above-described compatibility filter 36. Some embodiments may proceed to rank the filtered subset, as indicated by block 86, and present a recommended sequence of classes to administer to the patient based on the ranking, as indicated by block 88, for example, in the above-described display 18 with the user interface generator 40.

In some embodiments, some of the following steps may be performed by physician upon interacting with user interface. In some embodiments, the physician may determine whether there are more steps in the recommended sequence, as indicated by block 90. Upon determining that there are more steps, the physician may select a next class of pharmaceuticals in the sequence, as indicated by block 92. The physician may then cause the selected class of pharmaceuticals to be administered to the patient, as indicated by block 94, for instance, over some duration of time, which may span more than a week or month, and spanning multiple office visits in some cases. The physician may determine periodically whether to retest the patient, as indicated by block 96. Upon determining not to retest, the process may return to block 90 to determine whether there are further steps in the sequence to administer to the patient. Upon determining that there are no more steps in the sequence or upon determining to not retest, as indicated in block 90 or 96, some embodiments may terminate the process if the patient is healthy or return to block 52 to update the sequence based upon updated testing of the patient.

Figure 3:
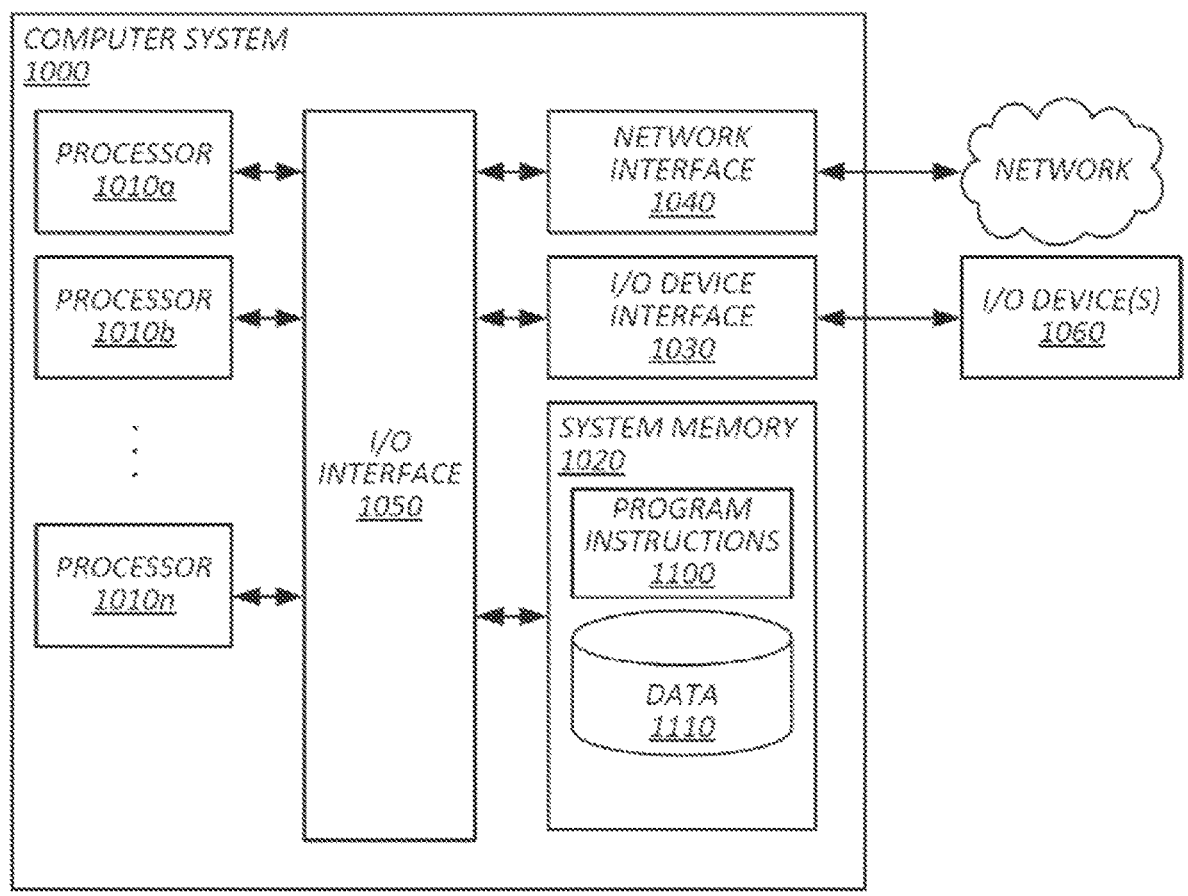
FIG. 3 is a block diagram of an example of a computing device upon which the application of FIG. 1 and process of FIG. 2 may be executed in accordance with some embodiments of the present techniques.

In some embodiments, the above techniques may be implemented with a specific approach described below in the following technical documentation. It should be emphasized of the technical documentation describes a subset of embodiments and does not purport to characterize all forms of implementation of the present approaches, which is not to suggest that any other description is so limiting:

FIG. 3 is a diagram that illustrates an exemplary computing system 1000 in accordance with embodiments of the present technique. Various portions of systems and methods described herein, may include or be executed on one or more computer systems similar to computing system 1000. Further, processes and modules described herein may be executed by one or more processing systems similar to that of computing system 1000.

Computing system 1000 may include one or more processors (e.g., processors 1010a-1010n) coupled to system memory 1020, an input/output I/O device interface 1030, and a network interface 1040 via an input/output (I/O) interface 1050. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing system 1000. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 1020). Computing system 1000 may be a uni-processor system including one processor (e.g., processor 1010a), or a multi-processor system including any number of suitable processors (e.g., 1010a-1010n). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computing system 1000 may include a plurality of computing devices (e.g., distributed computer systems) to implement various processing functions.

I/O device interface 1030 may provide an interface for connection of one or more I/O devices 1060 to computer system 1000. I/O devices may include devices that receive input (e.g., from a user) or output information (e.g., to a user). I/O devices 1060 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 1060 may be connected to computer system 1000 through a wired or wireless connection. I/O devices 1060 may be connected to computer system 1000 from a remote location. I/O devices 1060 located on remote computer system, for example, may be connected to computer system 1000 via a network and network interface 1040.

Network interface 1040 may include a network adapter that provides for connection of computer system 1000 to a network. Network interface may 1040 may facilitate data exchange between computer system 1000 and other devices connected to the network. Network interface 1040 may support wired or wireless communication. The network may include an electronic communication network, such as the Internet, a local area network (LAN), a wide area network (WAN), a cellular communications network, or the like.

System memory 1020 may be configured to store program instructions 1100 or data 1110. Program instructions 1100 may be executable by a processor (e.g., one or more of processors 1010a-1010n) to implement one or more embodiments of the present techniques. Instructions 1100 may include modules of computer program instructions for implementing one or more techniques described herein with regard to various processing modules. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 1020 may include a tangible program carrier having program instructions stored thereon. A tangible program carrier may include a non-transitory computer readable storage medium. A non-transitory computer readable storage medium may include a machine readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 1020 may include a non-transitory computer readable storage medium that may have program instructions stored thereon that are executable by a computer processor (e.g., one or more of processors 1010a-1010n) to cause the subject matter and the functional operations described herein. A memory (e.g., system memory 1020) may include a single memory device and/or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times.

I/O interface 1050 may be configured to coordinate I/O traffic between processors 1010a-1010n, system memory 1020, network interface 1040, I/O devices 1060, and/or other peripheral devices. I/O interface 1050 may perform protocol, timing, or other data transformations to convert data signals from one component (e.g., system memory 1020) into a format suitable for use by another component (e.g., processors 1010a-1010n). I/O interface 1050 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computer system 1000 or multiple computer systems 1000 configured to host different portions or instances of embodiments. Multiple computer systems 1000 may provide for parallel or sequential processing/execution of one or more portions of the techniques described herein.

Those skilled in the art will appreciate that computer system 1000 is merely illustrative and is not intended to limit the scope of the techniques described herein. Computer system 1000 may include any combination of devices or software that may perform or otherwise provide for the performance of the techniques described herein. For example, computer system 1000 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computer system 1000 may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 1000 may be transmitted to computer system 1000 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Similarly, reference to "a computer system" performing step A and "the computer system" performing step B can include the same computing device within the computer system performing both steps or different computing devices within the computer system performing steps A and B. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively. Computer implemented instructions, commands, and the like are not limited to executable code and can be implemented in the form of data that causes functionality to be invoked, e.g., in the form of arguments of a function or API call.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

The present techniques will be better understood with reference to the following enumerated embodiments:
1. A method, comprising: obtaining, with a computer system, test data that quantifies a patient's cardiovascular status, the test data specifying patient attributes in a plurality of cardiovascular dimensions of the patient, a first subset of the plurality of cardiovascular dimensions being independent cardiovascular dimensions and a second subset of the plurality of dimensions being dependent cardiovascular dimensions; determining, with the computer system, a plurality of normalized differences between the test data and target criteria in each of the cardiovascular dimensions, the plurality of normalized differences quantifying different aspects of hypertension of the patient; determining, with the computer system, predicted-effect vectors of each of a plurality of different classes of pharmaceuticals having hypertension as an indication, wherein: the predicted-effect vectors each correspond to a different respective class of pharmaceuticals among the different classes of pharmaceuticals, the predicted-effect vectors each have a plurality of values quantifying respective effects of the corresponding class of pharmaceuticals on corresponding dimensions among a third set of the cardiovascular dimensions of the patient, the values are each based on both the corresponding normalized differences of the corresponding dimension among the third set and a respective strength of effect of the corresponding class of pharmaceuticals on the corresponding dimension, the respective strength effects are determined based on respective multi-dimensional models of the corresponding class of pharmaceuticals, and the third set at least overlaps with the first subset and the second subset; determining, with the computer system, an aggregate score for each respective class of pharmaceuticals among the different classes of pharmaceuticals based on values of the corresponding predicted-effect vectors of the corresponding class of pharmaceuticals; ranking, with the computer system, the different classes of pharmaceuticals based on the aggregate scores to form a ranked list of the different classes of pharmaceuticals; and outputting, with the computer system, based on the ranking, a recommended sequence of the classes of pharmaceuticals to administer to the patient.

2. The method of embodiment 1, comprising: accessing, with the computer system, pair-wise compatibilities of the different classes of pharmaceuticals; and detecting, based on the -wise compatibilities, incompatible pairs of the different classes of pharmaceuticals in the ranked list; and removing, with the computer system, from the ranked list, at least one member of each detected incompatible pair to form a filtered, ranked list.

3. The method of embodiment 2, wherein: removing, with the computer system, at least one member from each detected pair comprises removing a lower-ranking member from each detected pair.

4. The method of embodiment 2, wherein forming a filtered, ranked list comprises obtaining, with the computer system, comorbidities or demographic information of the patient; and adjusting, with the computer system, the filtered, ranked list based on the obtained comorbidities or demographic information.

5. The method of embodiment 4, comprising: causing, with the computer system, a user interface to be presented, the user interface indicating a warning for a given one of the classes of pharmaceuticals in response to the comorbidities or demographic information.

6. The method of embodiment 2, comprising: administering a first class of pharmaceuticals at a first ranking in the filtered, ranked list; and after administering the first class of pharmaceuticals, administering a second class of pharmaceuticals at a second ranking in the filtered, ranked list, the second ranking being lower in the ranking than the first ranking.

7. The method of any one of embodiments 1-6 comprising: obtaining, with the computer system, a comorbidity or demographic attribute of the patient, wherein: a given one of the values of a given one of the predicted-effect vectors is based on the comorbidity or demographic attribute, at least some of the values of the given one of the predicted-effect vectors are not affected by the comorbidity or the demographic attribute, and at least some of the predicted-effect vectors are not affected by the comorbidity or the demographic attribute.

8. The method of any one of embodiments 1-7, wherein: the ranking is based on predicted-effect vector values corresponding to each of the first subset of dimensions.

9. The method of embodiment 8, wherein: the ranking is not based on predicted-effect vector values corresponding to any of the second subset of dimensions.

10. The method of embodiment 8, wherein: the first subset of dimensions includes at least two of the following dimensions: systolic blood pressure, pulse pressure, cardiac index, or heart rate.

11. The method of embodiment 8, wherein: the first subset of dimensions includes each of the following dimensions: systolic blood pressure, pulse pressure, cardiac index, and heart rate.

12. The method of any one of embodiments 1-11, wherein the classes of pharmaceuticals include at least six of the following: Diuretics, Beta-blockers, ACE inhibitors, Angiotensin II receptor blockers, Calcium channel blockers, Alpha blockers, Alpha-2 Receptor Agonists, Combined alpha and beta-blockers, Central agonists, Peripheral adrenergic inhibitors, or Vasodilators.

13. The method of any one of embodiments 1-11, wherein the classes of pharmaceuticals include each of the following: Diuretics, Beta-blockers, ACE inhibitors, Angiotensin II receptor blockers, Calcium channel blockers, Alpha blockers, Alpha-2 Receptor Agonists, Combined alpha and beta-blockers, Central agonists, Peripheral adrenergic inhibitors, and Vasodilators.

14. The method of any one of embodiments 1-13, wherein at least some of the plurality of normalized differences are z-scores specifying a number of standard deviations a corresponding patient attribute is in the test data from a mean of a population.

15. The method of any one of embodiments 1-13, wherein a given one of the aggregate scores for a given one of the classes of pharmaceuticals is based on a weighted sum of the values of the corresponding predicted-effect vector of the given one of the classes of pharmaceuticals.

16. The method of any one of embodiments 1-15, wherein at least some of the values are each based on products of the corresponding normalized differences of the corresponding dimension among the third set and the respective strength of effect of the corresponding class of pharmaceuticals on the corresponding dimension.

17. The method of any one of embodiments 1-16, wherein a given multi-dimensional model of a given one of the classes of pharmaceuticals specifies a non-planar surface in five or higher dimensions, the five or higher dimension comprising: an output dimension corresponding to an effect strength of the given one of the classes of pharmaceuticals, and four or more of the cardiovascular dimensions of the patient.

18. The method of any one of embodiments 1-17, comprising: repeating, with the computer system, the method of embodiment 1 with an updated instance of the test data obtained after administering part of the sequence of the classes of pharmaceuticals to the patient; and as a result of the repeating, changing, with the computer system, the sequence.

19. A tangible, non-transitory, machine-readable medium storing instructions that when executed by a data processing apparatus cause the data processing apparatus to perform operations comprising: the computer-implemented operations of any one of embodiments 1-18.

20. A system, comprising: one or more processors; and memory storing instructions that when executed by the processors cause the processors to effectuate operations comprising: the computer-implemented operations of any one of embodiments 1-18.

What is claimed is:

1. A tangible, non-transitory, machine-readable medium storing instructions that when executed by one or more processors effectuate operations comprising:
   obtaining, with an artificial intelligence (AI) application executed by a computer system, information about a current patient condition, wherein:
      the information relates to a patient who has undergone heart failure,
      at least some of the information is obtained from an electronic medical records system via an application program interface of the electronic medical records system,
      at least some of the information is validated or entered into the AI application by a medical professional after obtaining information from the electronic medical records system, and
      the AI application comprises:
         a plurality of pharmaceutical-specific models each corresponding to a different class of pharmaceuticals to treat heart failure, and
         an expert system comprising a plurality of rules in a rule-graph, the rule-graph being traversable to determine an updated prescription based on the patient condition and predicted patient responses from the pharmaceutical-specific models;
   inputting, with the computer system, at least some of the obtained information about the patient condition into the respective pharmaceutical-specific models and, in response:
      predicting respective changes in the condition of the patient responsive to respective changes in respective dosages of the respective classes of pharmaceuticals to obtain a set of predicted patient responses for the different classes of pharmaceutical,
      selecting based on the set of predicted patient responses, candidate classes of pharmaceuticals for an updated prescription,
      determining differences between target dosages and the current dosages of the classes of pharmaceuticals, and
      based on the differences, determining respective priority scores of the respective classes of pharmaceuticals;
   inputting, with the computer system, into the expert system of the AI application, the candidate classes of pharmaceuticals and their respective priority scores and, in response, determining an updated prescription; and
   storing, with the computer system, the updated prescription in memory.

2. The medium of claim 1, wherein the pharmaceutical-specific models comprise at least two of the following:
   an angiotensin-converting enzyme (ACE) inhibitor model,
   an angiotensin receptor blocker model,
   a beta-blocker model,
   a mineralocorticoid-receptor antagonist (MRA) model, or
   a renin-angiotensin-system (RAS) blocker model.

3. The medium of claim 1, wherein the pharmaceutical-specific models comprise each of the following:
   an angiotensin-converting enzyme (ACE) inhibitor model,p
   an angiotensin receptor blocker model,
   a beta-blocker model,
   a mineralocorticoid-receptor antagonist (MRA) model, and
   a renin-angiotensin-system (RAS) blocker model.

4. The medium of claim 1, wherein:
   at least some of the pharmaceutical-specific models comprise:
      a sub-model configured to determine a full-strength dosage of the respective class of pharmaceuticals for the patient based on the information about the current patient condition,
      an input configured to receive a current dosage of the respective class of pharmaceuticals for the patient from the information about the current patient condition, and
      a plurality of thresholds indicative of whether the current dosage is to be determined to be safe to increase, decrease, or leave unchanged for the patient; and
   the at least some of the pharmaceutical-specific models are configured to determine, based on the information about the current patient condition, a respective value indicative of whether the current dosage is determined to be safe and compare that value to the plurality of thresholds to determine whether to recommend a medical professional increase, decrease, or leave unchanged the current dosage.

5. The medium of claim 4, wherein the AI application is configured to determine that more than a threshold number of candidate classes of pharmaceuticals are determined to be candidates to be increased and, in response, select a subset of the candidate classes of pharmaceuticals to be increased based on respective determined priority scores of the subset of the candidate classes of pharmaceuticals.

6. The medium of claim 1, wherein:
   the AI application comprises a translator configured to translate a dosage of a given class of pharmaceuticals to a corresponding dosage of another class of pharmaceuticals; and
   a model specific to the another class of pharmaceuticals is configured to use the translated dosage to predict a patient response to changes in the another class of pharmaceuticals based on a current dosage in the given class of pharmaceuticals.

7. The medium of claim 1, wherein the AI application is configured to:
   determine a value indicative of a difference in heart rate between a target heart rate of the patient and a patient heart rate indicated in the information about the current patient condition; and
   adjust or otherwise determine at least some of the priority scores based on the value indicative of the difference in heart rate.

8. The medium of claim 1, wherein the AI application is configured to:
  determine a value indicative of a difference in thrombolytic predictive instrument (TPI) measurements between a target TPI measurement of the patient and a patient TPI measurement in the information about the current patient condition; and
  adjust or otherwise determine at least some priority scores based on the value indicative of the difference in TPI measurements.

9. The medium of claim 1, wherein at least some of the pharmaceutical-specific models comprise:
  means for determining whether the respective class of pharmaceuticals is suitable for the patient; and
  means for determining a priority of the respective class of pharmaceuticals.

10. The medium of claim 1, wherein the expert system comprises:
  a plurality of rules encoded as Boolean statements corresponding to nodes and edges of the rule-graph; and
  a rules engine configured to:
    traverse the rule-graph by evaluating the Boolean statements based the candidate classes of pharmaceuticals and their respective determined priority scores, and
    output an updated prescription based on the evaluating.

11. The medium of claim 1, wherein the expert system comprises a plurality of rules including at least two of the following:
  a rule responsive to whether fluid flow in the patient is negative;
  a rule responsive to whether fluid flow in the patient is neutral;
  a rule responsive to whether the patient is taking an antiarrhythmic agent;
  a rule responsive to whether to whether the patient has experienced atrial fibrillation;
  a rule responsive to an whether a threshold amount of dosages of different classes of pharmaceuticals are candidates to be changed concurrently; or
  a rule that adjusts the threshold amount of dosages of different classes of pharmaceuticals based on a blood sugar level of the patient in the information about the current patient condition.

12. The medium of claim 1, wherein the expert system comprises a plurality of rules including each of the following:
  a rule responsive to whether fluid flow in the patient is negative;
  a rule responsive to whether fluid flow in the patient is neutral;
  a rule responsive to whether the patient is taking an antiarrhythmic agent;
  a rule responsive to whether to whether the patient has experienced atrial fibrillation;
  a rule responsive to an whether a threshold amount of dosages of different classes of pharmaceuticals are candidates to be changed concurrently; and
  a rule that adjusts the threshold amount of dosages of different classes of pharmaceuticals based on a blood sugar level of the patient in the information about the current patient condition.

13. The medium of claim 1, wherein the expert system comprises a plurality of rules including each of the following:
  a rule that takes a variable;
  a rule that modifies a value of a variable in another rule conditional upon inputs;
  a rule that outputs a recommendation conditional upon inputs; and
  a rule that that outputs a prohibition conditional upon inputs.

14. The medium of claim 1, wherein:
  the expert system comprises more than 250 rules;
  the prescription is updated more than 5 times for a given patient;
  the number of prescription-specific models is greater than or equal to 4; and
  the AI model is responsive to more than 10 different lab test measurements and demographic attributes.

15. The medium of claim 1, wherein the expert system comprises rules encoding:
  steps for determining a response to a beta negative flow of the patient.

16. The medium of claim 1, wherein the expert system comprises rules encoding:
  steps for determining a response to use of sotalol by the patient.

17. The medium of claim 1, wherein the expert system comprises rules encoding:
  steps for determining a response to a fluid negative flow of the patient.

18. The medium of claim 1, wherein the AI application is configured to present a recommended updated prescription in a user interface based on output of the expert system.

19. The medium of claim 1, wherein the information about the patient comprises:
  impedance cardiograph data based upon variation in impedance measurements during heart beats from an alternating current applied to a set of four or more electrodes placed on the patient adjacent a neck of the patient and a diaphragm of the patient;
  age and gender of the patient;
  a value indicative of use of a loop diuretic with the patient; and
  values indicative of results of at least three of the following tests of the patient:
    a measurement of B-type natriuretic peptide (BNP) in blood of the patient,
    a measurement of N-terminal pro-BNP in blood of the patient,
    a metabolic panel indicative of an amount of electrolyte imbalance, kidney failure, or liver disease of the patient,
    a complete blood count (CBC) indicative of anemia,
    a thyroid tests indicative of an amount of thyroid hormone in blood of the patient,
    a measurement of Galectin-3 protein in blood of the patient, or
    a measurement of ST2 protein in blood of the patient.

20. A method, comprising:
  obtaining, with an artificial intelligence (AI) application executed by a computer system, information about a current patient condition, wherein:
    the information relates to a patient who has undergone heart failure,
    at least some of the information is obtained from an electronic medical records system via an application program interface of the electronic medical records system, at least some of the information is validated or entered into the AI application by a medical professional after obtaining information from the electronic medical records system, and the AI application comprises:
   a plurality of pharmaceutical-specific models each corresponding to a different class of pharmaceuticals to treat heart failure, and
   an expert system comprising a plurality of rules in a rule-graph, the rule-graph being traversable to determine an updated prescription based on the patient condition and predicted patient responses from the pharmaceutical-specific models;

inputting, with the computer system, at least some of the obtained information about the patient condition into the respective pharmaceutical-specific models and, in response:
   predicting respective changes in the condition of the patient responsive to respective changes in respective dosages of the respective classes of pharmaceuticals to obtain a set of predicted patient responses for the different classes of pharmaceutical,
   selecting based on the set of predicted patient responses, candidate classes of pharmaceuticals for an updated prescription,
   determining differences between target dosages and the current dosages of the classes of pharmaceuticals, and
   based on the differences, determining respective priority scores of the respective classes of pharmaceuticals;

inputting, with the computer system, into the expert system of the AI application, the candidate classes of pharmaceuticals and their respective priority scores and, in response, determining an updated prescription; and storing, with the computer system, the updated prescription in memory.

21. The method of claim 20, wherein the pharmaceutical-specific models comprise at least two of the following:
   an angiotensin-converting enzyme (ACE) inhibitor model,
   an angiotensin receptor blocker model,
   a beta-blocker model,
   a mineralocorticoid-receptor antagonist (MRA) model, or
   a renin-angiotensin-system (RAS) blocker model.

22. The method of claim 20, wherein the pharmaceutical-specific models comprise each of the following:
   an angiotensin-converting enzyme (ACE) inhibitor model,p
   an angiotensin receptor blocker model,
   a beta-blocker model,
   a mineralocorticoid-receptor antagonist (MRA) model, and
   a renin-angiotensin-system (RAS) blocker model.

23. The method of claim 20, wherein:
at least some of the pharmaceutical-specific models comprise:
   a sub-model configured to determine a full-strength dosage of the respective class of pharmaceuticals for the patient based on the information about the current patient condition,
   an input configured to receive a current dosage of the respective class of pharmaceuticals for the patient from the information about the current patient condition, and
   a plurality of thresholds indicative of whether the current dosage is to be determined to be safe to increase, decrease, or leave unchanged for the patient; and the at least some of the pharmaceutical-specific models are configured to determine, based on the information about the current patient condition, a respective value indicative of whether the current dosage is determined to be safe and compare that value to the plurality of thresholds to determine whether to recommend a medical professional increase, decrease, or leave unchanged the current dosage.

24. The method of claim 20, wherein:
the AI application comprises a translator configured to translate a dosage of a given class of pharmaceuticals to a corresponding dosage of another class of pharmaceuticals; and
a model specific to the another class of pharmaceuticals is configured to use the translated dosage to predict a patient response to changes in the another class of pharmaceuticals based on a current dosage in the given class of pharmaceuticals.

25. The method of claim 23, wherein the AI application is configured to determine that more than a threshold number of candidate classes of pharmaceuticals are determined to be candidates to be increased and, in response, select a subset of the candidate classes of pharmaceuticals to be increased based on respective determined priority scores of the subset of the candidate classes of pharmaceuticals.

26. The method of claim 20, wherein the AI application is configured to:
   determine a value indicative of a difference in heart rate between a target heart rate of the patient and a patient heart rate indicated in the information about the current patient condition; and
   adjust or otherwise determine at least some of the priority scores based on the value indicative of the difference in heart rate.

27. The method of claim 20, wherein the AI application is configured to:
   determine a value indicative of a difference in thrombolytic predictive instrument (TPI) measurements between a target TPI measurement of the patient and a patient TPI measurement in the information about the current patient condition; and
   adjust or otherwise determine at least some priority scores based on the value indicative of the difference in TPI measurements.

28. The method of claim 20, wherein at least some of the pharmaceutical-specific models comprise:
   means for determining whether the respective class of pharmaceuticals is suitable for the patient; and
   means for determining a priority of the respective class of pharmaceuticals.

29. The method of claim 20, wherein the expert system comprises:
   a plurality of rules encoded as Boolean statements corresponding to nodes and edges of the rule-graph; and
   a rules engine configured to:
      traverse the rule-graph by evaluating the Boolean statements based the candidate classes of pharmaceuticals and their respective determined priority scores, and
      output an updated prescription based on the evaluating.

30. The method of claim 20, wherein the expert system comprises a plurality of rules including at least two of the following:

a rule responsive to whether fluid flow in the patient is negative;

a rule responsive to whether fluid flow in the patient is neutral;

a rule responsive to whether the patient is taking an antiarrhythmic agent;

a rule responsive to whether to whether the patient has experienced atrial fibrillation;

a rule responsive to an whether a threshold amount of dosages of different classes of pharmaceuticals are candidates to be changed concurrently; or a rule that adjusts the threshold amount of dosages of different classes of pharmaceuticals based on a blood sugar level of the patient in the information about the current patient condition.

31. The method of claim 20, wherein the expert system comprises a plurality of rules including each of the following:

a rule responsive to whether fluid flow in the patient is negative;

a rule responsive to whether fluid flow in the patient is neutral;

a rule responsive to whether the patient is taking an antiarrhythmic agent;

a rule responsive to whether to whether the patient has experienced atrial fibrillation;

a rule responsive to an whether a threshold amount of dosages of different classes of pharmaceuticals are candidates to be changed concurrently; and a rule that adjusts the threshold amount of dosages of different classes of pharmaceuticals based on a blood sugar level of the patient in the information about the current patient condition.

32. The method of claim 20, wherein the expert system comprises a plurality of rules including each of the following:

a rule that takes a variable;

a rule that modifies a value of a variable in another rule conditional upon inputs;

a rule that outputs a recommendation conditional upon inputs; and a rule that that outputs a prohibition conditional upon inputs.

33. The method of claim 20, wherein:

the expert system comprises more than 250 rules;

the prescription is updated more than 5 times for a given patient;

the number of prescription-specific models is greater than or equal to 4; and the AI model is responsive to more than 10 different lab test measurements and demographic attributes.

34. The method of claim 20, wherein the expert system comprises rules encoding:

steps for determining a response to a beta negative flow of the patient.

35. The method of claim 20, wherein the expert system comprises rules encoding:

steps for determining a response to use of sotalol by the patient.

36. The method of claim 20, wherein the expert system comprises rules encoding:

steps for determining a response to a fluid negative flow of the patient.

37. The method of claim 20, wherein the AI application is configured to present a recommended updated prescription in a user interface based on output of the expert system.

38. The method of claim 20, wherein the information about the patient comprises:

impedance cardiograph data based upon variation in impedance measurements during heart beats from an alternating current applied to a set of four or more electrodes placed on the patient adjacent a neck of the patient and a diaphragm of the patient;

age and gender of the patient;

a value indicative of use of a loop diuretic with the patient; and values indicative of results of at least three of the following tests of the patient:

a measurement of B-type natriuretic peptide (BNP) in blood of the patient, a measurement of N-terminal pro-BNP in blood of the patient, a metabolic panel indicative of an amount of electrolyte imbalance, kidney failure, or liver disease of the patient, a complete blood count (CBC) indicative of anemia, a thyroid tests indicative of an amount of thyroid hormone in blood of the patient, a measurement of Galectin-3 protein in blood of the patient, or a measurement of ST2 protein in blood of the patient.

* * * * *